United States Patent
Schachar

(10) Patent No.: US 6,299,640 B1
(45) Date of Patent: Oct. 9, 2001

(54) SCLERAL PROSTHESIS FOR TREATMENT OF PRESBYOPIA AND OTHER EYE DISORDERS

(75) Inventor: Ronald A. Schachar, Dallas, TX (US)

(73) Assignee: R A S Holding Corp, Dallas, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 09/472,535

(22) Filed: Dec. 27, 1999

Related U.S. Application Data

(63) Continuation of application No. 08/946,975, filed on Oct. 8, 1997, now Pat. No. 6,007,578.

(51) Int. Cl.[7] .................................................. A61F 2/14
(52) U.S. Cl. ............................................................ 623/4.1
(58) Field of Search ............................................... 623/4.1

(56) References Cited

U.S. PATENT DOCUMENTS

| | | | |
|---|---|---|---|
| Re. 35,390 | 12/1996 | Smith | 604/8 |
| 3,064,643 | 11/1962 | Dixon | 128/76.5 |
| 4,521,210 | 6/1985 | Wong | 604/8 |
| 4,946,436 | 8/1990 | Smith | 604/8 |
| 4,976,719 | 12/1990 | Siepser | 606/151 |
| 5,354,331 | 10/1994 | Schachar | 623/4 |
| 5,443,505 | 8/1995 | Wong et al. | 623/4 |
| 5,520,631 | 5/1996 | Nordquist et al. | 604/8 |
| 5,558,630 | 9/1996 | Fisher | 604/8 |
| 5,766,242 | 6/1998 | Wong et al. | 623/4 |
| 6,007,578 | * 12/1999 | Schachar | 623/4.1 |

FOREIGN PATENT DOCUMENTS

2784287 * 10/1998 (FR).

* cited by examiner

Primary Examiner—Dinh X. Nguyen

(57) ABSTRACT

Presbyopia is treated by implanting within a plurality of elongated pockets formed in the tissue of the sclera of the eye transverse to a meridian of the eye, a prosthesis having an elongated base member having an inward surface adapted to be placed against the inward wall of the pocket and having a ridge on the inward surface of the base extending along at least a major portion of the major dimension of the base. The combined effect of the implanted prostheses is to exert a radially outward traction on the sclera in the region overlying the ciliary body which expands the sclera in the affected region together with the underlying ciliary body. The expansion of the ciliary body restores the effective working distance of the ciliary muscle in the presbyopic eye and thereby increases the amplitude of accommodation. Hyperopia, primary open angle glaucoma and/or ocular hypertension can be treated by increasing the effective working distance of the ciliary muscle according to the invention.

20 Claims, 10 Drawing Sheets

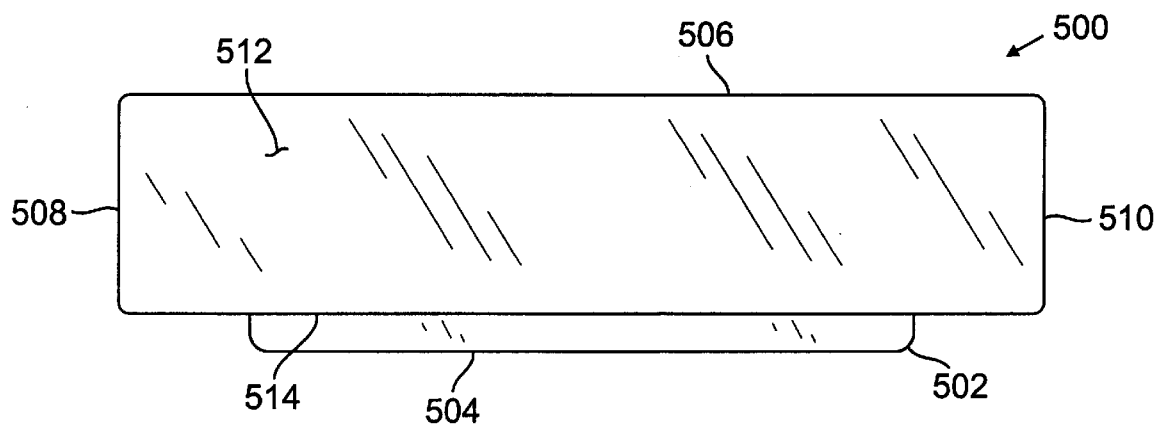
FIG. 14
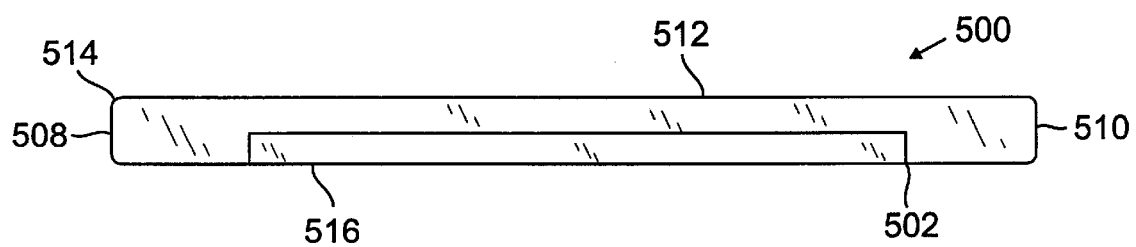
FIG. 15
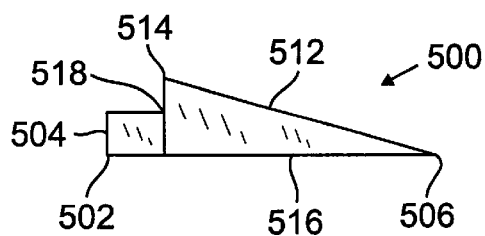  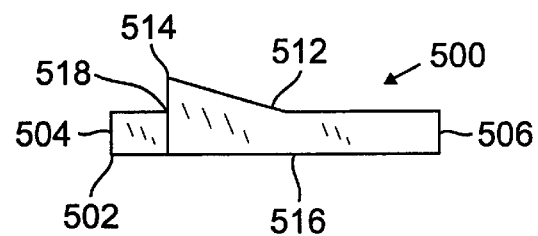
FIG. 16a          FIG. 16b

SCLERAL PROSTHESIS FOR TREATMENT OF PRESBYOPIA AND OTHER EYE DISORDERS

This application is a continuation of prior U.S. application Ser. No. 08/946,975 filed on Oct. 8, 1997 U.S. Pat. No. 6,007,578.

BACKGROUND OF THE INVENTION

1. Field of the Invention

This invention relates to methods of treating presbyopia, hyperopia, primary open angle glaucoma and ocular hypertension and more particularly to methods of treating these diseases by increasing the effective working distance of the ciliary muscle. The invention also relates to increasing the amplitude of accommodation of the eye by increasing the effective working range of the ciliary muscle.

2. Brief Description of the Prior Art

In order for the human eye to have clear vision of objects at different distances, the effective focal length of the eye must be adjusted to keep the image of the object focused as sharply as possible on the retina. This change in effective focal length is known as accommodation and is accomplished in the eye by varying the shape of the crystalline lens. Generally, in the unaccommodated emmetropic eye the curvature of the lens is such that distant objects are sharply imaged on the retina. In the unaccommodated eye near objects are not focused sharply on the retina because their images lie behind the retinal surface. In order to visualize a near object clearly, the curvature of the crystalline lens is increased, thereby increasing its refractive power and causing the image of the near object to fall on the retina.

The change in shape of the crystalline lens is accomplished by the action of certain muscles and structures within the eyeball or globe of the eye. The lens is located in the forward part of the eye, immediately behind the pupil. It has the shape of a classical biconvex optical lens, i.e., it has a generally circular cross section having two convex refracting surfaces, and is located generally on the optical axis of the eye, i.e., a straight line drawn from the center of the cornea to the macula in the retina at the posterior portion of the globe. In the unaccommodated human eye the curvature of the posterior surface of the lens, i.e., the surface adjacent to the vitreous body, is somewhat greater than that of the anterior surface. The lens is closely surrounded by a membranous capsule that serves as an intermediate structure in the support and actuation of the lens. The lens and its capsule are suspended on the optical axis behind the pupil by a circular assembly of very many radially directed elastic fibers, the zonules, which are attached at their inner ends to the lens capsule and at their outer ends to the ciliary muscle, a muscular ring of tissue, located just within the outer supporting structure of the eye, the sclera. The ciliary muscle is relaxed in the unaccommodated eye and therefore assumes its largest diameter. According to the classical theory of accommodation, originating with Helmholtz, the relatively large diameter of the ciliary muscle in this condition causes a tension on the zonules which in turn pulls radially outward on the lens capsule, causing the equatorial diameter of the lens to increase slightly and decreasing the anterior-posterior dimension of the lens at the optical axis. Thus, the tension on the lens capsule causes the lens to assume a flattened state wherein the curvature of the anterior surface, and to some extent the posterior surface, is less than it would be in the absence of the tension. In this state the refractive power of the lens is relatively low and the eye is focused for clear vision for distant objects.

When the eye is intended to be focused on a near object, the ciliary muscles contract. According to the classical theory, this contraction causes the ciliary muscle to move forward and inward, thereby relaxing the outward pull of the zonules on the equator of the lens capsule. This reduced zonular tension allows the elastic capsule of the lens to contract causing an increase in the antero-posterior diameter of the lens (i.e., the lens becomes more spherical) resulting in an increase in the optical power of the lens. Because of topographical differences in the thickness of the lens capsule, the central anterior radius of curvature decreases more than the central posterior radius of curvature. This is the accommodated condition of the eye wherein the image of near objects falls sharply on the retina.

Presbyopia is the universal decrease in the amplitude of accommodation that is typically observed in individuals over 40 years of age. In the person having normal vision, i.e., having emmetropic eyes, the ability to focus on near objects is gradually lost, and the individual comes to need glasses for tasks requiring near vision, such as reading.

According to the conventional view the amplitude of accommodation of the aging eye is decreased because of the loss of elasticity of the lens capsule and/or sclerosis of the lens with age. Consequently, even though the radial tension on the zonules is relaxed by contraction of the ciliary muscles, the lens does not assume a greater curvature. According to the conventional view, it is not possible by any treatment to restore the accommodative power to the presbyopic eye. The loss of elasticity of the lens and capsule is seen as irreversible, and the only solution to the problems presented by presbyopia is to use corrective lenses for close work, or bifocal lenses, if corrective lenses are also required for distant vision.

Certain rings and/or segments have been used in ocular surgery for various purposes. Rings and/or segments of flexible and/or elastic material, attached or prepared in situ by fastening the ends of strips of the material around the posterior portion of the globe, posterior to the pars plana (over the underlying retina), have been used to compress the sclera in certain posterior regions. Supporting rings of metal, adapted to fit the contour of the sclera have been used as temporary supporting structures during surgery on the globe. However, none of these known devices have been used for surgical treatment of presbyopia, and none have been adapted to the special needs of prosthetic devices used in treating presbyopia.

Accordingly, a need has continued to exist for a method of treating presbyopia that will increase the amplitude of accommodation of the presbyopic eye, thereby lessening or eliminating the need for auxiliary spectacle lenses to relieve the problems of presbyopia.

SUMMARY OF THE INVENTION

The treatment of presbyopia has now been facilitated by the prosthetic device of this invention which is implanted within a pocket formed in the sclera of the globe of the eye in the vicinity of the plane of the equator of the crystalline lens. The prosthetic device of the invention comprises a base, having an elongated planform, and a ridge extending along at least a major portion of the elongated planform. The prosthesis is inserted into the scleral pocket with the base oriented in a generally outward direction from the center of the globe, and the ridge directed inwardly. The anterior edge of the prosthesis accordingly applies an outward force on the anterior edge of the scleral pocket which elevates the portion of the sclera attached thereto and the ciliary body immediately beneath the sclera to increase the working distance of the ciliary muscle according to the theory of the inventor.

Accordingly, it is an object of the invention to provide a treatment for presbyopia.

A further object is to provide a treatment for presbyopia by increasing the effective working distance of the ciliary muscle in the presbyopic eye.

A further object is to provide a treatment for presbyopia by increasing the radial distance between the equator of the crystalline lens and the ciliary body.

A further object is to provide a treatment for presbyopia by implanting in the sclera a plurality of prostheses which will increase the working distance of the ciliary muscle A further object is to provide a treatment for hyperopia.

A further object is to provide a treatment for primary open angle glaucoma.

A further object is to provide a treatment for ocular hypertension.

A further object is to provide a treatment for increasing the amplitude of accommodation of the eye.

Further objects of the invention will become apparent from the description of the invention which follows.

BRIEF DESCRIPTION OF THE DRAWINGS

FIG. 14 illustrates a plan view of an embodiment of the invention in which the ridge member extends beyond the end of the base member.

FIG. 15 shows a front elevational view of the prosthesis illustrated in FIG. 14.

FIG. 16a shows an end elevational view of the prosthesis of FIG. 14, wherein the base prosthesis is tapered to the posterior edge.

FIG. 16b shows an end elevational view of a prosthesis similar to that shown in FIGS. 14, 15 and 16a, wherein the base is not tapered.

DETAILED DESCRIPTION OF THE INVENTION AND PREFERRED EMBODIMENTS

Figure 1:
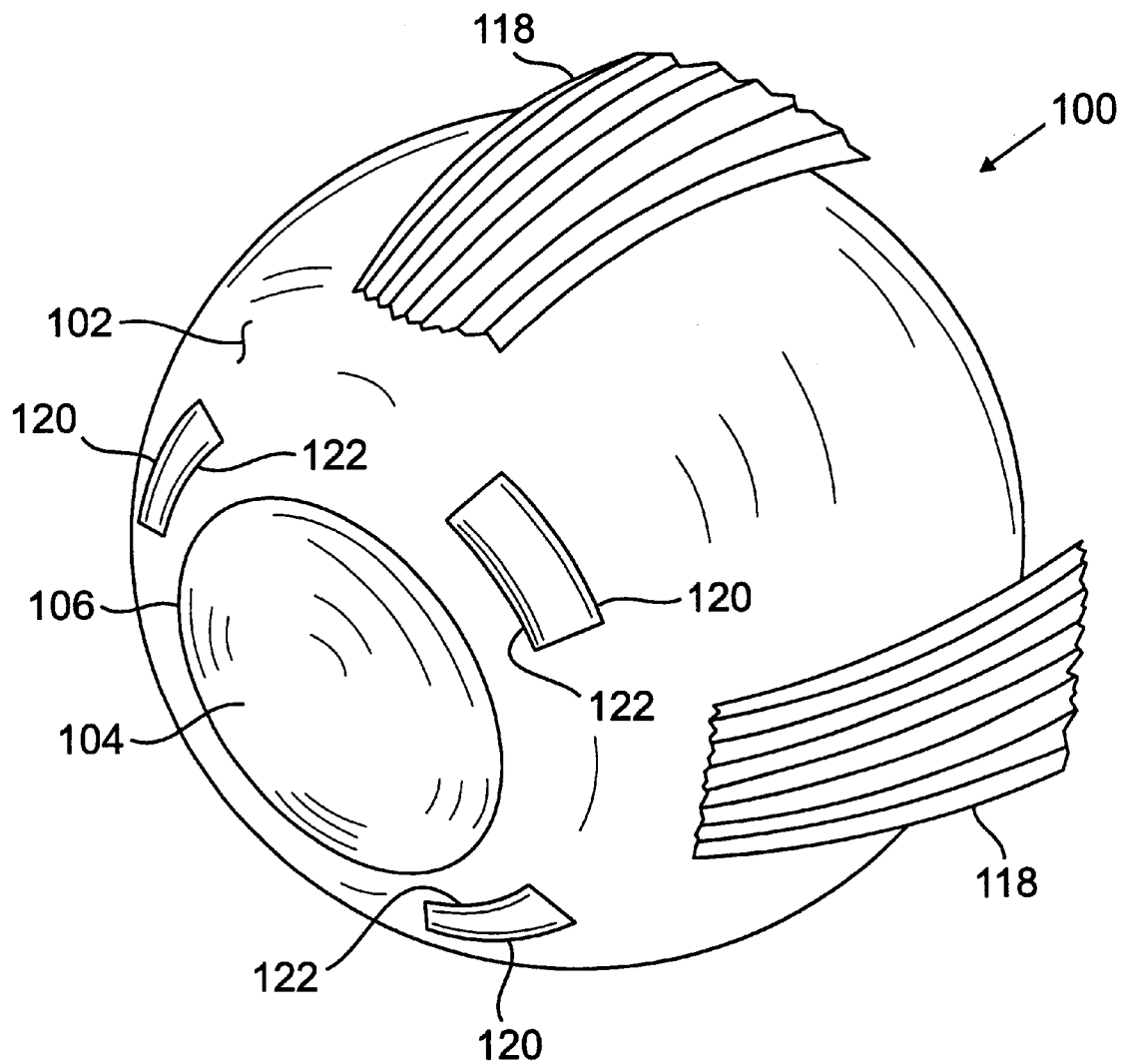
FIG. 1 shows an isometric view of an eye having the prosthesis of this invention implanted therein.

This invention is based on a different theory, developed by the inventor, which has been described in U.S. Pat. No. 5,354,331, the entire disclosure of which is incorporated herein by reference, regarding the cause of the loss of amplitude of accommodation that constitutes presbyopia. According to the invention, presbyopia is treated by increasing the effective working distance of the ciliary muscle. This is accomplished by increasing the distance between the ciliary muscle and the lens equator by increasing the diameter of the sclera in the region of the ciliary body.

According to the invention the effective working distance of the ciliary muscle is increased by implanting in pockets surgically formed in the sclera of the eye a plurality of prostheses designed to place an outward traction on the sclera in the region of the ciliary body. The relevant anatomy of the eye for locating the scleral pockets may be seen by reference to FIGS. 1–4. The outermost layer of the eye 100 comprises the white, tough sclera 102 which encompasses most of the globe and the transparent cornea 104, which constitutes the anterior segment of the outer coat. The circular junction of the cornea and sclera is the limbus 106. Within the globe of the eye, as illustrated in the cross-section of FIG. 4, the crystalline lens 108 is enclosed in a thin membranous capsule and is located immediately posterior to the iris 112, suspended centrally posterior to the pupil 114 on the optical axis of the eye. The lens 108 is suspended by zonules extending between the lens capsule at the equator 110 of the lens 108 and the ciliary body 116. The ciliary body 116 lies just under the sclera 102 (i.e., just inwardly of the sclera 102) and is attached to the inner surface of the sclera 102. As may be seen in FIG. 4, the ciliary body 116 lies generally in a plane 130 defined by the equator 110 of the lens 108. The plane 130 can also be extended to intersect the sclera 102 whereby it forms a generally circular intersection located about 2 millimeters posterior to the limbus 106. The external muscles 118 of the eyeball control the movement of the eye.

According to the invention a generally outwardly directed traction is exerted on the sclera in the region of the ciliary body to expand the sclera 102 in that region. This expansion of the sclera 102 produces a corresponding expansion of the attached ciliary body 116 and moves the ciliary body 116 outwardly away from the equator of the lens 108, generally in the plane 130 of the equator 110 of the lens 108. The sclera 102 is preferably expanded, approximately in the plane of the equator of the lens 108. However, any expansion of the sclera 102 in the region of the ciliary body 116, i.e., in the region of the sclera somewhat anterior or posterior to the plane of the equator 110 of the lens 108 is within the scope of the invention, provided that such expansion of the sclera 102 moves the ciliary body 116 away from the equator 110 of the lens 108. Typically, the expansion of the sclera will be accomplished in the region from about 1.5 millimeters anterior to the plane 130 of the equator of the lens 108 to about 2.5 millimeters posterior to that plane, i.e., from about 0.5 millimeters to about 4.5 millimeters posterior to the limbus 106. Accordingly, the anterior margin 122 of a scleral pocket 120 will be located in that region of the sclera.

The prosthesis of the invention is designed to apply an outwardly directed traction to the sclera at the general position of the anterior margin 122 of a scleral pocket 120. Accordingly, the prosthesis of the invention has a base adapted to be placed against the outer wall of the pocket surgically formed in the sclera. The base has an elongated planform and is oriented generally circumferentially with respect to the circle defined on the sclera by the intersection therewith of the plane 130 of the equator 110 of the lens 108.

Figure 4:
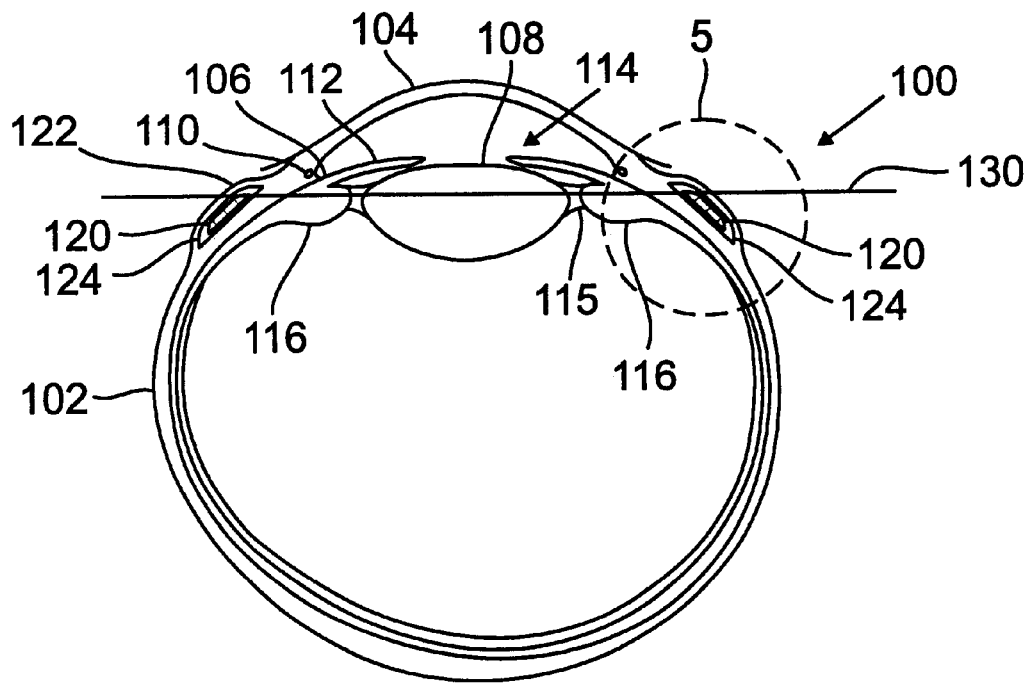
FIG. 4 shows a cross section of the eye of FIG. 2 along the line 4—4.
Figure 5:
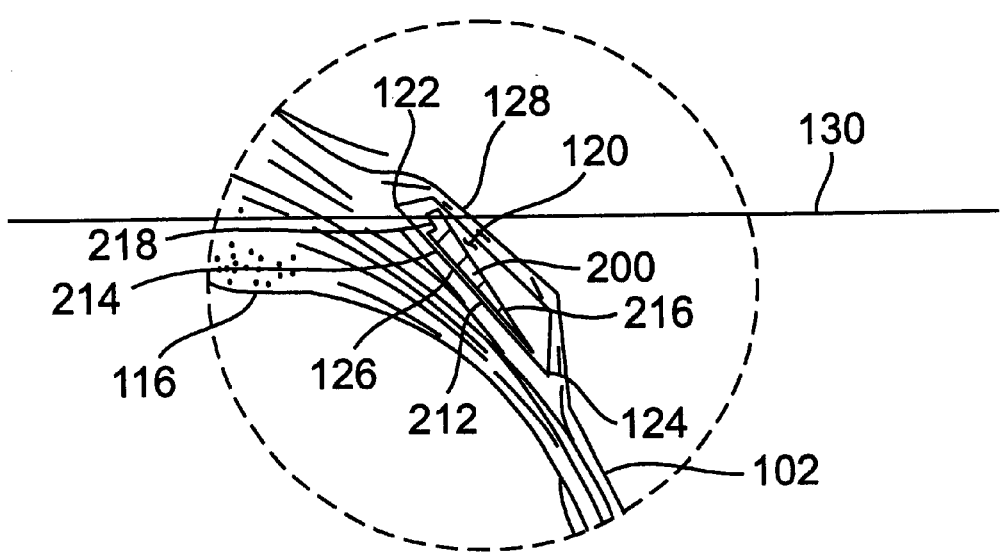
FIG. 5 shows an enlarged view of the cross section of FIG. 4 in the region indicated by the circle 5.
Figure 6:
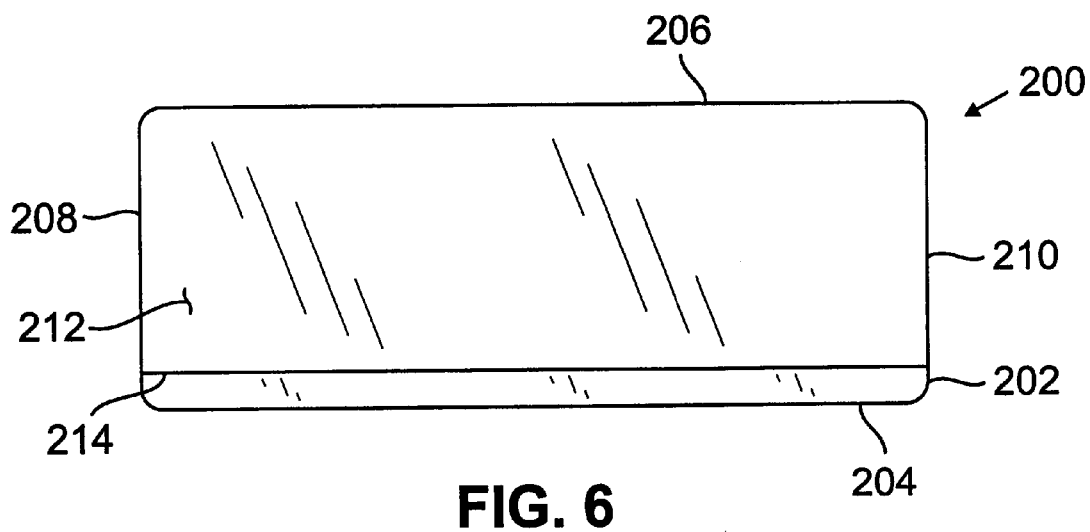
FIG. 6 shows a plan view of a rectangular embodiment of the prosthesis of the invention having a flat base.
Figure 7:
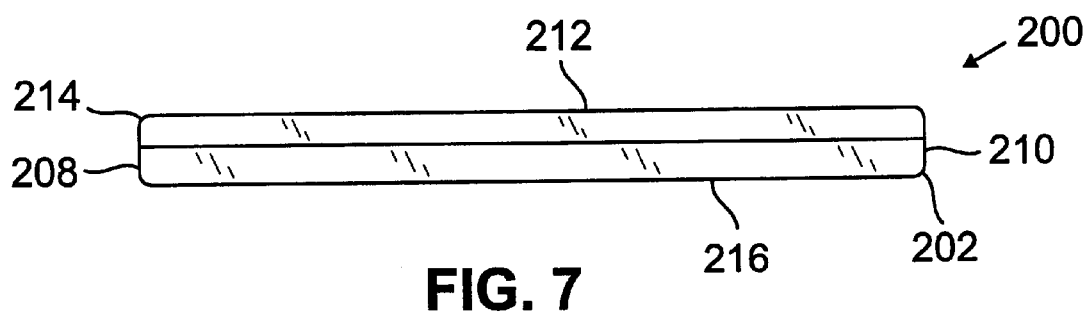
FIG. 7 shows a front elevational view of the prosthesis illustrated in FIG. 6.
Figure 8:
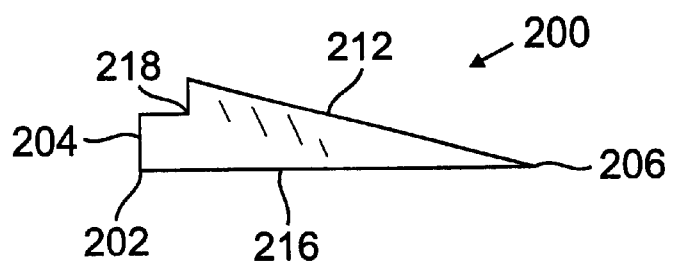
FIG. 8 shows an end elevational view of the prosthesis shown in FIG. 6.

The position of the prosthesis within a scleral pocket and its operation to expand the sclera are illustrated in FIGS. 4 and 5, showing a prosthesis of the type illustrated in FIGS. 6–8.

The base member 202 of the prosthesis 200 has a smooth exterior face 216 adapted to be placed in contact with the internal surface of the outer wall 128 of the scleral pocket 120. The opposite, or interior, face 212 of the prosthesis 200 is provided with a ridge 214 extending along a substantial portion of the length of the base 202. This ridge bears against the inner wall 126 of the scleral pocket 120. Accordingly, the sclera 102 at the anterior margin 122 of the scleral pocket 120 is elevated above its original level. The attached ciliary body 116 is thereby also expanded away from the equator 110 of the lens 108, and the working distance of the ciliary muscle is increased.

A first embodiment of the prosthesis of the invention is illustrated in FIGS. 6–8. FIG. 6 shows a plan view of the inner face of the prosthesis 200 having a base 202 with an anterior edge 204, a posterior edge 206, and lateral ends 208 and 210. The inner face 212 is provided with a ridge 214 extending along the length of the major dimension of the elongated base 202. FIG. 7 shows a front elevational view of the prosthesis of FIG. 6 showing the flat, smooth outer surface 216 of the prosthesis. FIG. 8 shows a side view of the prosthesis showing the outer surface 216, the ridge 214 and a notch 218 on the inner surface 212 of the prosthesis.

Figure 3:
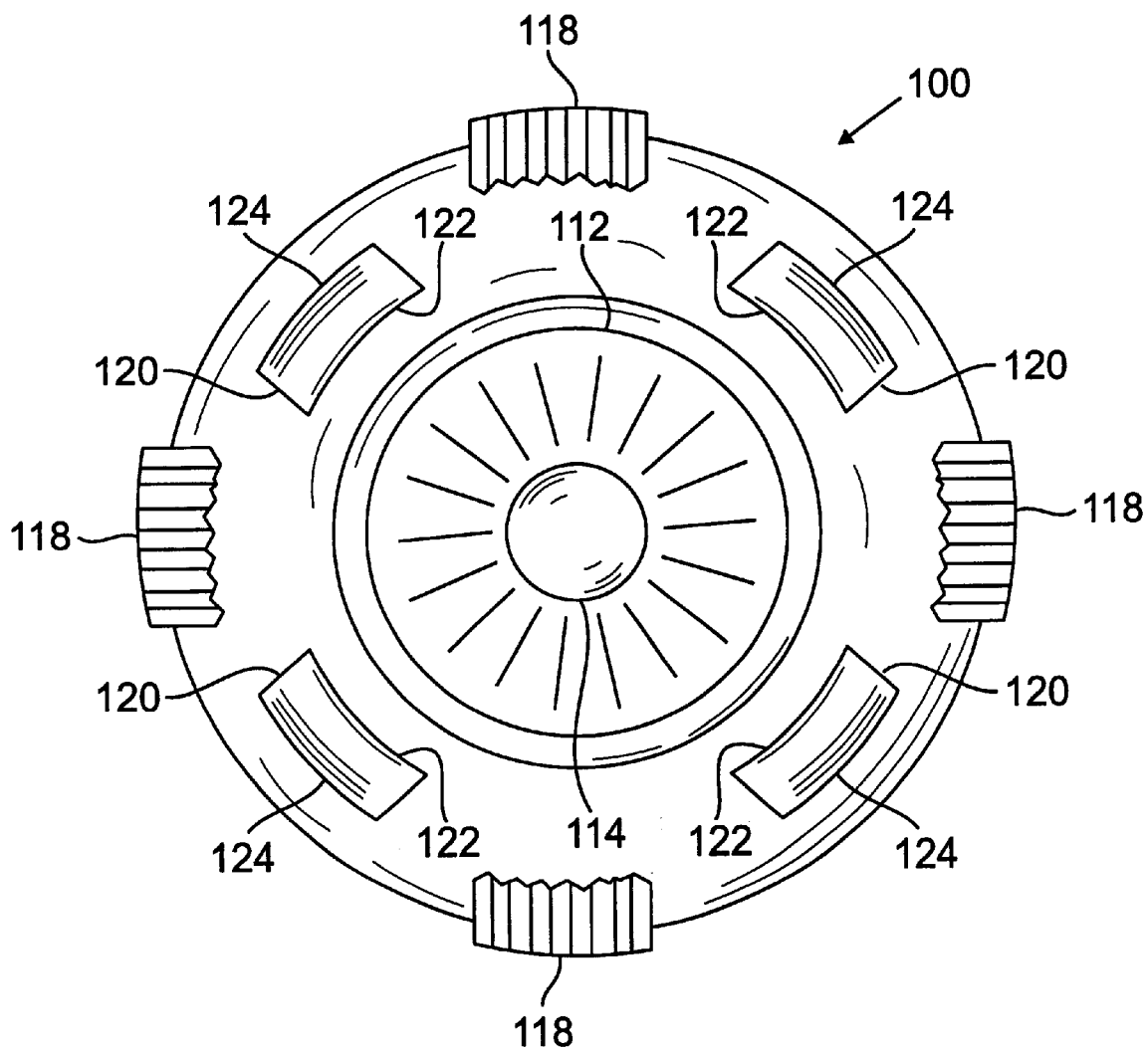
FIG. 3 shows a front elevational view of an eye showing the location of straight scleral pockets.
Figure 9:
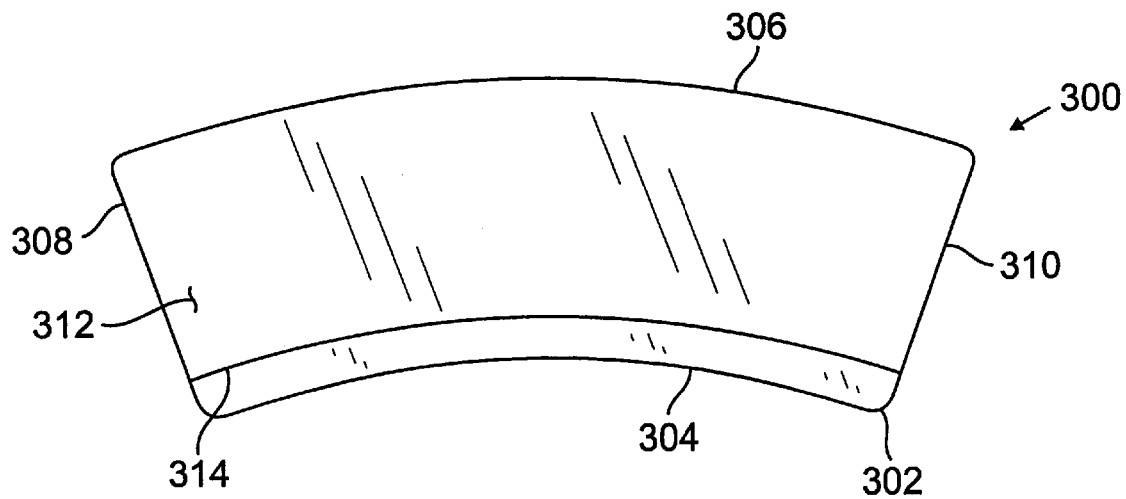
FIG. 9 shows a plan view of an embodiment of the prosthesis that is curved in the plane of the base.
Figure 10:
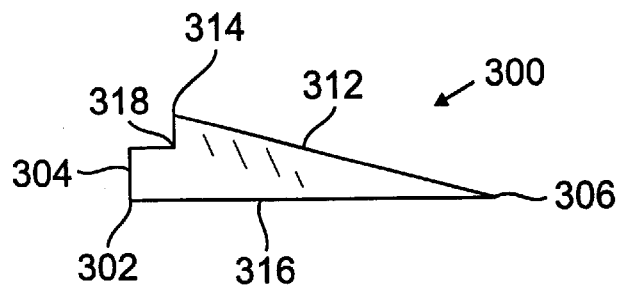
FIG. 10 shows an end view of the prosthesis of FIG. 9.

FIGS. 9–10 illustrate a prosthesis of the invention having a curved planform adapted to be implanted in a scleral pocket that is curved to match the curvature of the eyeball. The prosthesis 300 of FIGS. 9–10 has a generally planar base 302, curved in the plane of the base 302, having an anterior edge 304, a posterior edge 306, and lateral ends 308 and 310. The inner face 312 is provided with a ridge 314 extending along the length of the major dimension of the elongated curved base 302. FIG. 10 shows an side view of the prosthesis of FIG. 9 showing the outer face 316, the ridge 314 and a notch 318 on the inner face 312 of the prosthesis. The curvature of the base is chosen to provide at least an approximate match for the curvature of the adjacent structures on the surface of the sclera, e.g., the limbus 106, adjusted for the distance of the scleral pocket 120 and prosthesis 300 from the limbus 106. FIG. 3 shows a front elevational view of an eye provide with curved scleral pockets 120 to accommodate a curved prosthesis 300 of the type illustrated in FIGS. 9 and 10.

Figure 11:
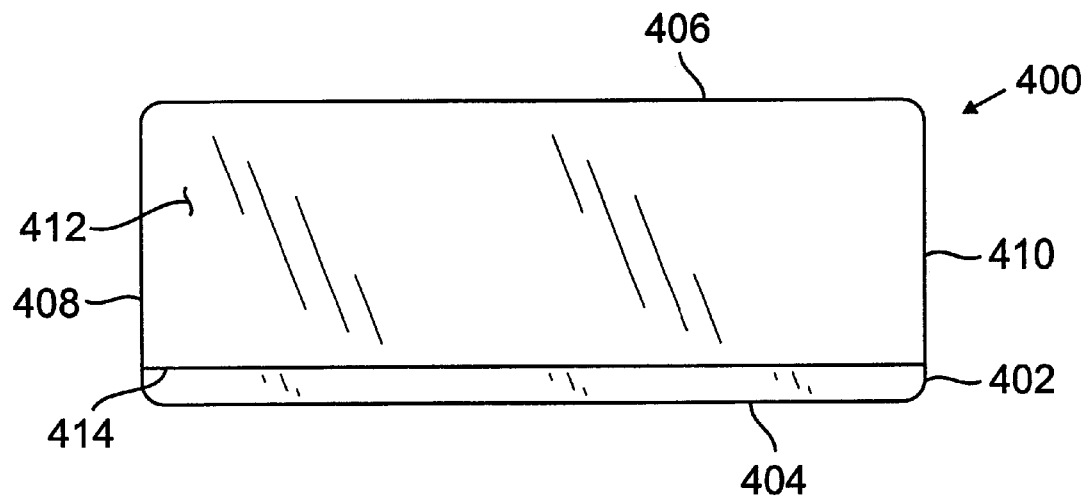
FIG. 11 illustrates a plan view of an alternate embodiment of the prosthesis of the invention.
Figure 12:
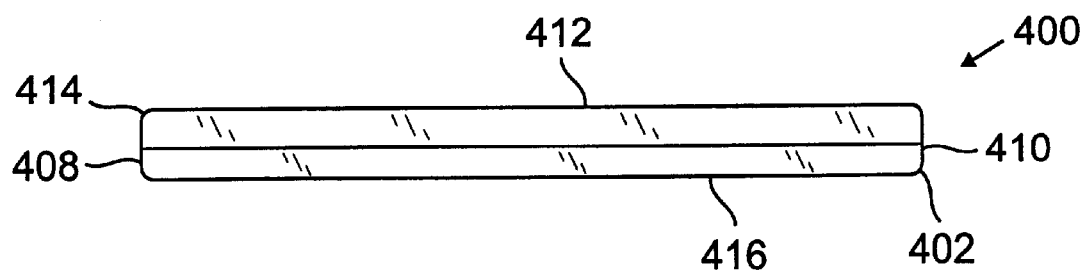
FIG. 12 shows a front elevational view of the prosthesis illustrated in FIG. 11.
Figure 13:
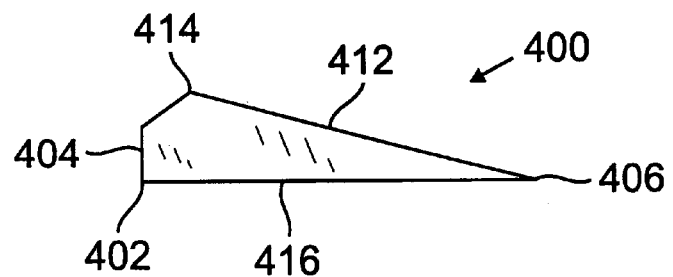
FIG. 13 shows an end elevational view of the prosthesis of FIG. 11.

FIGS. 11–13 show an embodiment of the invention wherein the anterior portion is tapered from the ridge to the anterior edge. FIG. 11 shows a plan view of the prosthesis 400 having a base 402 with an anterior edge 404, a posterior edge 406, and lateral ends 408 and 410. The outer face 416 is smooth and adapted to be placed against the inner surface of the outer wall 128 of a scleral pocket 120. The inner face 412 is provided with a ridge 414 extending along the length of the major dimension of the elongated base 402. FIG. 12 shows a front elevational view of the prosthesis of FIG. 11 showing the flat, smooth outer face 412 of the prosthesis. FIG. 13 shows an end view of the prosthesis of FIG. 11 showing the outer face 412 and the ridge 414 on the inner face 412 of the prosthesis 400. In this embodiment the ridge 414 tapers toward the anterior edge 404 of the prosthesis.

FIGS. 14–16 show a preferred embodiment of the prosthesis in which the ridge member includes extensions beyond the ends of the base member which lie on the surface of the sclera adjacent to the scleral pocket and help to stabilize the prosthesis. FIG. 14 shows a plan view of this embodiment 500 having a base 502 with an anterior edge 504, a posterior edge 506, and lateral ends 508 and 510. The inner face 512 is provided with a ridge 514. The ends 508 and 510 of the base 502 extend slightly beyond the ends of the ridge 514. Accordingly, the ends 508 and 510 of the base 502 will extend beyond the ends of the pocket 120 and lie on the surface of the sclera 102. FIG. 15 shows a front elevational view of the prosthesis of FIG. 14 showing the flat, smooth outer face 516 of the prosthesis and the ends 508 and 510 of the base 502 extending beyond the ends of the ridge 514. FIG. 16a shows an end view of the prosthesis of FIG. 14 showing the smooth outer face 516 and the ridge 514 on the inner face 512 of the base 502, as well as a notch 518. FIG. 16b shows and end view of an alternate embodiment of the prosthesis 500 wherein the base 502 does not taper all the way to the posterior edge 506. Evidently, the thickness of the posterior edge 506 may vary from a relatively sharp posterior edge as shown in FIG. 16a to a relatively thick posterior edge as shown in FIG. 16b, or even thicker if it is advantageous.

Figure 17:
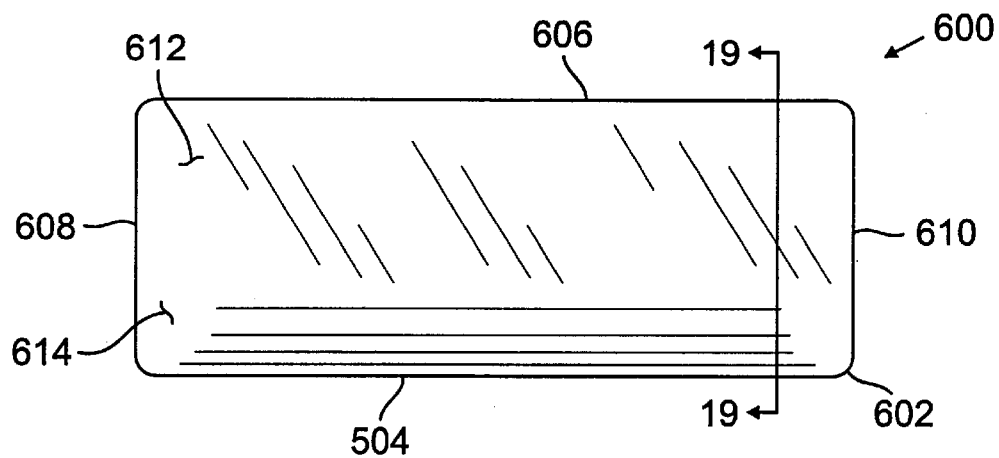
FIG. 17 shows a plan view of an embodiment of the prosthesis of the invention wherein the prosthesis is hollow and made of an elastomeric material that is filled with a liquid.
Figure 18:
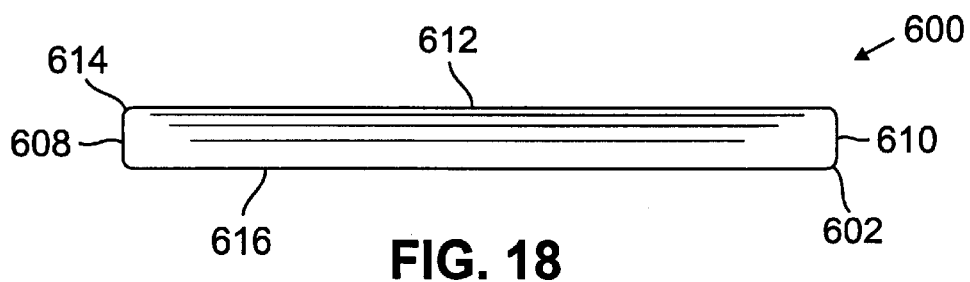
FIG. 18 shows a front elevational view of the prosthesis illustrated in FIG. 17.
Figure 19:
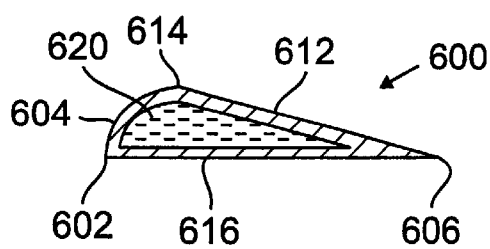
FIG. 19 shows a cross sectional view of the prosthesis of FIG. 17 along the line 19—19.
Figure 20:
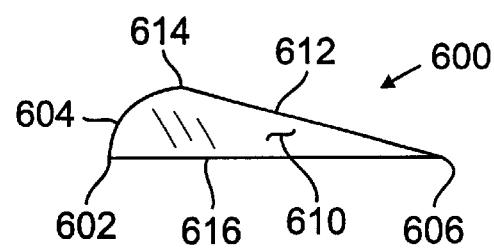
FIG. 20 shows an end elevational view of the prosthesis of FIG. 17.

FIGS. 17–20 illustrate an embodiment of the prosthesis that is hollow and made from a plastic or elastomeric material and filled with a liquid. FIG. 17 shows a plan view of this embodiment 600 having a base 602 with an anterior edge 604, a posterior edge 606, and lateral ends 608 and 610. The inner face 612 is smoothly rounded and rises to a crest 614 that serves to support the prosthesis on the inner wall 126 of the scleral pocket 120 in the same way as the ridge member of other embodiments of the invention. FIG. 18 shows a front elevational view of the prosthesis of FIG. 17 showing the flat, smooth outer face 614 of the prosthesis. FIG. 19 shows a cross section of the prosthesis of FIG. 17 taken along the line 19—19. The cross-section shows the flexible wall 612 of the prosthesis as well as the flat outer face 616, and the crest 614. The cross section also shows the filling liquid 620. FIG. 20 shows an end view of the prosthesis of FIG. 17 showing the outer face 616 and the crest or ridge 614 on the inner face 612 of the prosthesis 600. The hollow prosthesis is filled with liquid, typically by injecting the liquid through an end 608 or 610. The prosthesis may be filled with more or less liquid in order to adjust the thickness between the outer face 616 and the crest or ridge 614 to provide more or less traction on the sclera at the anterior margin 122 of the scleral pocket or belt loop 120.

Figure 21:
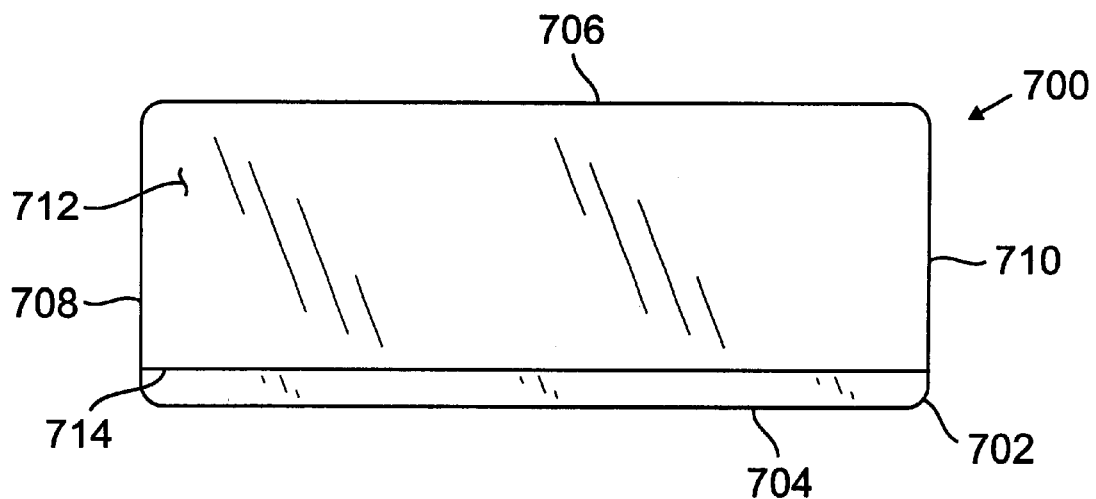
FIG. 21 illustrates a plan view of an embodiment of the prosthesis of the invention wherein the base is curved to match the curvature of the globe.
Figure 22:
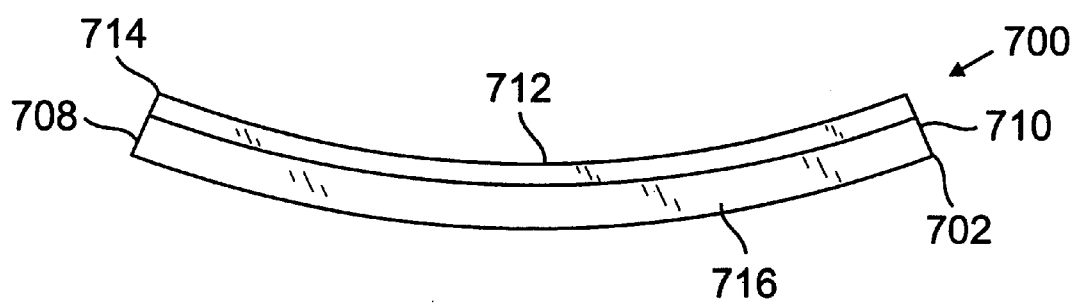
FIG. 22 shows a front elevational view of the prosthesis illustrated in FIG. 21.
Figure 23:
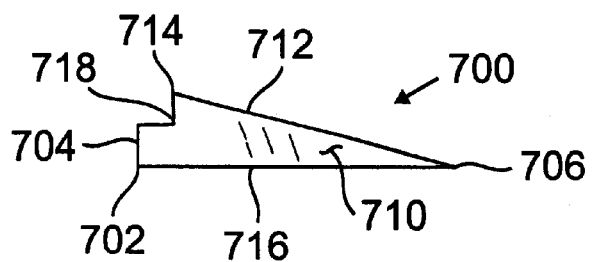
FIG. 23 shows an end elevational view of the prosthesis of FIG. 21.

FIGS. 21–23 illustrate an embodiment of the invention generally similar to that shown in FIGS. 6–8, having, however, a base in which the inner face of the prosthesis is curved to provide an approximate match to the curvature of the globe. FIG. 21 shows a plan view of the inner face of the prosthesis 700 having a base 702 with an anterior edge 704, a posterior edge 706, and lateral ends 708 and 710. The inner face 712 is provided with a ridge 714 extending along the length of the major dimension of the elongated base 716. FIG. 22 shows a front elevational view of the prosthesis of FIG. 21 showing the curved, smooth outer surface 716 of the prosthesis. FIG. 23 shows an end view of the prosthesis showing the outer surface 716, the ridge 714 and a notch 718 on the curved inner surface 712 of the prosthesis.

A preferred embodiment of the scleral prosthesis is that shown in FIGS. 9 and 10, wherein the anterior rim 304 and the posterior rim 306 are both generally circular arcs. The taper in the diameter of the segment is preferably selected in an individual case to fit the globe in the region of the ciliary body. Accordingly, different sizes of segments will be provided wherein the radius of curvature of the anterior rim ranges from about 7.0 to about 10 millimeters in 0.50 millimeter increments. Accordingly, a preferred segment has a typical internal circular radius of curvature at its anterior portion of about 7.76 millimeters, at the position of the ridge of about 8.21 millimeters, and at the posterior rim of about 8.91 millimeters. The preferred segment has outer radius of curvature at its anterior portion of 8.02 millimeters, at its mid portion 8.47 millimeters, and at its base 8.94 millimeters. These measurements will vary depending on the size of the eye, the amount of rigidity required, and the strength of the material from which the segment is made. The preferred anterior chord length of the segment is 5 millimeters. The axial width of the segment will typically be about 2 millimeters.

The scleral prosthesis of the invention is made of a material that is sufficiently rigid to exert a force on the sclera sufficient to produce the radial expansion required by the method of the invention and that is physiologically acceptable for long-term implantation or contact with the ocular tissues. Such materials are well-known in the surgical art and include suitable metals, ceramics, and synthetic resins. Suitable metals include titanium, gold, platinum, stainless steel, tantalum and various surgically acceptable alloys, and the like. Suitable ceramics may include crystalline and vitreous materials such as porcelain, alumina, silica, silicon carbide, high-strength glasses and the like. Suitable synthetic materials include physiologically inert materials such as poly(methyl methacrylate), polyethylene, polypropylene, poly(tetrafluoroethylene), polycarbonate, silicone resins and the like. The prosthesis may also be made of composite materials incorporating a synthetic resin or other matrix reinforced with fibers of high strength material such as glass fibers, boron fibers or the like. Thus, the segment may be made of glass-fiber-reinforced epoxy resin, carbon fiber-reinforced epoxy resin, carbon fiber-reinforced carbon (carbon-carbon), or the like. The segment may be made of a semi-rigid exterior and a liquid or gel filled interior so that the internal and external dimensions can be altered by injecting various amounts of liquid: water, saline, or silicone oil; or various amounts of a gel: silicone, collagen, or gelatin. The semi-rigid exterior may be made of any of the already listed materials. A preferred material for the entire segment is surgical grade poly(methyl methacrylate).

The scleral prosthesis of the invention may be manufactured by any conventional technique appropriate to the material used, such as machining, injection molding, heat molding, compression molding and the like.

The scleral prosthesis may be foldable to facilitate insertion into a scleral belt loop or made in a plurality of parts so that it can be assembled prior to use or may be installed separately to form a complete prosthesis.

In practicing the method of the invention, the surgeon locates the proper region of the sclera to be expanded by measuring a distance of preferably 2.0 millimeters posterior of the limbus. At 2.5 millimeters clockwise and counter-clockwise from each of the 45° meridians of the eye, and 2 millimeters posterior to the limbus, partial scleral thickness radial incisions, i.e., antero-posterior incisions, are made which are 2 millimeters long and 350 microns deep. Using a lamella blade the sclera is dissected until the partial thickness incisions are connected so that four scleral pockets or belt loops are made which have an anterior length of 5 millimeters, and a length extending generally axially of the eye of 2 millimeters. Thus, each pocket or belt loop is preferably centered over the 45° meridian of the eye. A prosthesis is then inserted in each of the four scleral belt loops. This produces symmetrical scleral expansion which will produce the desired result of increasing the effective working distance of the ciliary muscle.

The location of the prostheses of the invention when implanted in the eye is illustrated in FIGS. 1–4. FIG. 1 is an isometric view of an eye 100 having a globe 102 with the relevant exterior anatomical parts indicated as discussed above.

Figure 2:
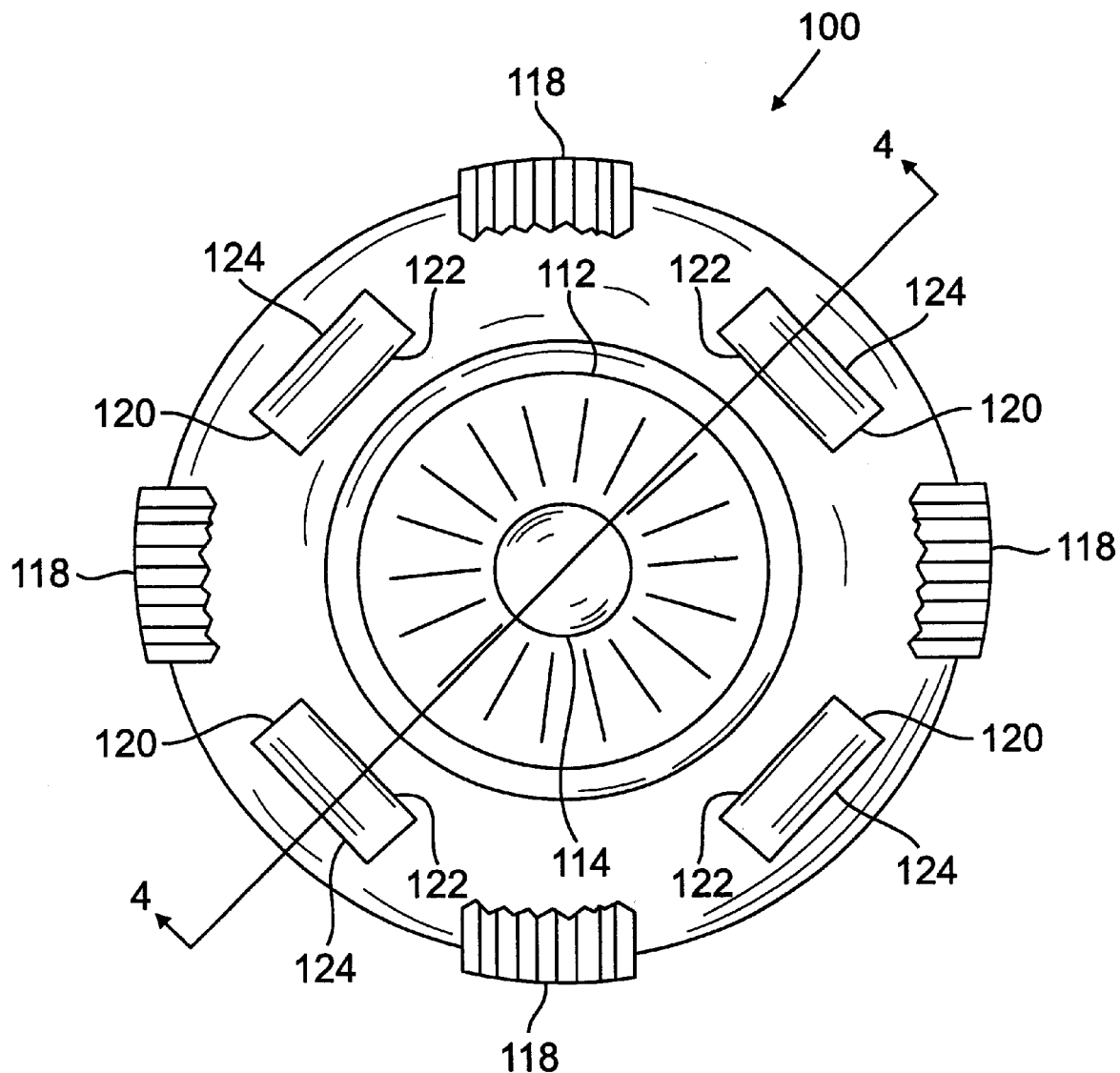
FIG. 2 shows a front elevational view of an eye showing the location of straight scleral pockets.

FIGS. 2 and 3 show front elevational views of an eye 100 showing the scleral pockets 120 formed at approximately the 45° meridians of the eye, i.e., approximately halfway between the vertical and horizontal meridians of the globe. This location is preferred because it avoids interference with structures of the eye that are located generally on the vertical and horizontal meridians. FIG. 3 shows the use of curved scleral pockets 120 to permit the use of curved prostheses of the type illustrated in FIGS. 9 and 10. FIG. 2 shows the use of straight scleral pockets 120. Such straight pockets are somewhat simpler to prepare surgically. For many patients the use of straight prostheses can provide adequate treatment of their presbyopia.

FIG. 4 shows a cross-section of the eye, taken along the line 4—4 in FIG. 3, showing the placement of the prosthesis of the invention relative to the significant anatomical structures of the eye. This figure shows the general configuration of the scleral pockets 120 and the prostheses 200 of the type illustrated in FIGS. 6–8 in a preferred embodiment. The anterior margins 122 of the scleral pockets or belt loops 120 are located approximately in the plane 130 of the equator 110 of the lens 108. The ridge 210 of the prosthesis causes the anterior portion of the pocket to be expanded somewhat more than the posterior portion. This places the sclera at the anterior margin of the pocket under a radial tension and causes it to expand somewhat from its normal diameter at that position. This scleral expansion draws with it the underlying ciliary body 116 and causes the ciliary body to be drawn away from the equator 110 of the lens 108. Accordingly, the expansion of the ciliary body 116 operates to increase the working distance of the ciliary muscle and restore, at least in part, the ability of the eye to accommodate for clear focusing on objects at different distances. FIG. 5 shows an enlarged portion of one of the scleral pockets 120 with adjacent anatomical structures. It shows the relation of the scleral pocket 120 to the underlying structures and its location just posterior to the equator of the lens 108 and overlying the ciliary body 116.

The method of the invention which increases the amplitude of accommodation may also be of benefit in treatment of hyperopia in certain patients. Some youthful hyperopes can achieve relatively normal vision by compensating for their hyperopia through the natural accommodative ability of the eye. However, as this ability declines with age, they find that it becomes more difficult to attain normal vision by this process, and they begin to experience headaches and other symptoms, even at an age somewhat less than usual for the onset of presbyopia. Evidently, increasing the amplitude of accommodation by the method of this invention would be useful in restoring the ability of these patients to compensate for their hyperopia.

The method of this invention also has utility in the treatment of primary open-angle glaucoma, which shows a correlation with age in certain individuals. It has been found that, in general, intraocular pressure (IOP) exhibits a linear increase with increasing age. (Armaly, M. F., On the distribution of applanation pressure I. Statistical features and the effect of age, sex, and family history of glaucoma, Archives of Ophthalmology, Vol. 73, pp. 11–18 (1965)). Among the general population is found a group of individuals who develop abnormally high intraocular pressures as a result of primary open angle glaucoma, a disease which is one of the most prevalent causes of blindness in the world. According to the theory of this invention, the linear increase in IOP with age is a direct result of the decrease in distance between the lens equator and the ciliary muscle and the resulting linear decrease in the effective pull of the ciliary muscle. Since the ciliary muscle inserts into the trabecular meshwork, the decrease in pull will decrease the size of the trabeculum and/or the drainage pores and result in a linear increase of intraocular pressure with age. In this view, the patients who develop primary open angle glaucoma may have a congenital predilection to narrower pores, protein deposition in the pores, and/or a smaller trabecular meshwork, so that when the ability of the ciliary muscle to exert force declines, after the age of 40 or thereabouts, they tend to develop excessively elevated IOP.

The method of the invention which increases the effective working distance of the ciliary muscle, and thereby increases the force that it can exert when it contracts, restores the level of force which the ciliary muscle exerts on the trabecular meshwork to a value characteristic of a more youthful eye. In this way it is expected that the tendency of an eye that is disposed to develop primary open angle glaucoma as it ages would be overcome and the onset of this disease would be prevented or at least postponed.

The invention having now been fully described, it should be understood that it may be embodied in other specific forms or variations without departing from its spirit or essential characteristics. Accordingly, the embodiments described above are to be considered in all respects as illustrative and not restrictive, the scope of the invention being indicated by the appended claims rather than the foregoing description, and all changes which come within the meaning and range of equivalency of the claims are intended to be embraced therein.

I claim:

1. A prosthesis adapted for contact with the sclera of an eyeball, said prosthesis comprising an elongated base having a first end and a second end and means for expanding said contacted sclera to increase the effective working distance of the ciliary muscle of the eyeball.

2. The prosthesis set forth in claim 1 wherein said expanding means is one of a ridge and a crest.

3. The prosthesis set forth in claim 1 wherein said base further comprises an outer surface that is generally smooth and is adapted to contact ocular tissue within a pocket surgically formed within the sclera of the eyeball.

4. The prosthesis set forth in claim 1 wherein said prosthesis is one of generally rectangular, semicircular, and elliptical.

5. The prosthesis set forth in claim 1 wherein said base further comprises an anterior edge and a posterior edge, and said expanding means has a maximum height above said base of one of intermediate between said anterior edge and said posterior edge, less than halfway from said anterior edge to said posterior edge, and at said anterior edge.

6. The prosthesis set forth in claim 1 wherein said base further comprises a planform having a first dimension, a second dimension, an inner surface and an outer surface.

7. The prosthesis set forth in claim 6 wherein said outer surface of said base is planar.

8. The prosthesis set forth in claim 6 wherein said expanding means extends along at least a portion of said first dimension of said base.

9. The prosthesis set forth in claim 6 wherein one of said first dimension is about 5 millimeters and said second dimension is about 2 millimeters.

10. The prosthesis set forth in claim 1 wherein said prosthesis is made of one of a physiologically acceptable metal, a ceramic material, a synthetic resin, a reinforced composite material, and a flexible material.

11. The prosthesis set forth in claim 1 wherein said prosthesis is provided with an internal cavity.

12. The prosthesis set forth in claim 11 wherein said internal cavity is filled with one of a fluid and a gel.

13. The prosthesis set forth in claim 11 wherein said internal cavity is filled with one of water, a saline solution, an oil, silicone, collagen, and gelatin.

14. A prosthesis adapted for surgical implant into a pocket in the sclera of an eyeball, said prosthesis comprising an elongated base having a first end and a second end and one of a ridge and a crest, said implanted prosthesis applying an outward force on said scleral pocket to elevate the portion of the sclera attached thereto to increase the effective working distance of the ciliary muscle of the eyeball.

15. The prosthesis set forth in claim 14 wherein said base further comprises an outer surface that is generally smooth and is adapted to contact ocular tissue within the scleral pocket.

16. The prosthesis set forth in claim 14 wherein said prosthesis is one of generally rectangular, semicircular, and elliptical.

17. The prosthesis set forth in claim 14 wherein said base further comprises an anterior edge and a posterior edge, and said prosthesis has a maximum height above said base of one of intermediate between said anterior edge and said posterior edge, less than halfway from said anterior edge to said posterior edge, and at said anterior edge.

18. The prosthesis set forth in claim 14 wherein said base further comprises a planform having a first dimension, a second dimension, an inner surface and an outer surface.

19. The prosthesis set forth in claim 18 wherein said outer surface of said base is planar.

20. A prosthesis adapted for contact with the sclera of an eyeball, said prosthesis comprising an elongated base having a first end and a second end and one of a ridge and a crest, said prosthesis expanding said contacted sclera to increase the effective working distance of the ciliary muscle of the eyeball.

* * * * *